US00PP34189P2

(12) United States Plant Patent
Brinkmann

(10) Patent No.: US PP34,189 P2
(45) Date of Patent: May 3, 2022

(54) RASPBERRY PLANT NAMED 'PLAPINK 14116'

(50) Latin Name: ***Rubus idaeus* L.**
Varietal Denomination: Plapink 14116

(71) Applicant: Plantas de Navarra, S.A. Sociedad Unipersonal, Valtierra (ES)

(72) Inventor: Michael Brinkmann, Navarra (ES)

(73) Assignee: Plantas de Navarra, S.A. Sociedad Unipersonal, Navarra (ES)

( * ) Notice: Subject to any disclaimer, the term of this patent is extended or adjusted under 35 U.S.C. 154(b) by 0 days.

(21) Appl. No.: 17/381,627

(22) Filed: Jul. 21, 2021

(30) Foreign Application Priority Data

Oct. 6, 2020 (QZ) ..... PBR 2020/2450
Dec. 28, 2020 (MA) ..... PBR 1036/20
Jan. 6, 2021 (MX) ..... PBR 3340

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./203, 204
See application file for complete search history.

*Primary Examiner* — Susan McCormick Ewoldt
(74) *Attorney, Agent, or Firm* — Knobbe, Martens, Olson & Bear, LLP

(57) ABSTRACT

The new raspberry variety 'Plapink 14116' is characterized by a combination of traits which include, but are not limited to, a medium to dense spine density and the very abundant production of light-red colored, conical-shaped, medium-size fruit having medium firmness. 'Plapink 14116' is a self-fertile variety.

17 Drawing Sheets

Botanical classification: *Rubus idaeus* L.
Variety denomination: 'Plapink 14116'.

CROSS-REFERENCE TO RELATED APPLICATIONS

This application claims the benefit of European Community Plant Variety Office Application No. 2020/2450, filed on Oct. 6, 2020, Moroccan Plant Variety Application No. 1036/20, filed Dec. 28, 2020, and Mexican Plant Variety Application No. 3340, filed Jan. 6, 2021, each of which is incorporated by reference herein in its entirety.

BACKGROUND

Disclosed herein is a new and distinct raspberry variety. The varietal denomination of the new variety is 'Plapink 14116'. The new variety was designated by the breeder as breeder number '14.26R.04'. The new variety of raspberry was created in a breeding program by crossing two parents. The seed parent was an undistributed raspberry variety designated '10.05R.05' (unpatented) and the pollen parent was an undistributed raspberry parent designated '07.09R.47' (unpatented). Each parent was a selection from a breeder's program and has not been commercialized.

The resulting seedling of the new variety was grown and asexually propagated by Michael Brinkmann by root cuttings in Segovia, Spain, 3° 59'W., 41° 22'N., 2742 feet elevation. Clones of the new variety were further asexually propagated and extensively tested. This propagation and testing demonstrated that the combination of traits disclosed herein which characterize the new variety are fixed and retained true to type through successive generations of asexual reproduction.

The new variety 'Plapink 14116' is characterized by a vigorous plant with consistent fruit production from beginning of October through the end of December on primocanes and in the ensuing year beginning in April and again beginning in June. In addition, the new variety has an upright plant habit and very abundant production of light-red colored (RHS Red group color near 41 B to 41 C), conical-shaped, large-sized fruit having strong glossiness.

COMPARISON TO THE PARENT VARIETIES

The new variety is distinguished from the parental varieties by the following characteristics possessed by 'Plapink 14116' which are different than, or not possessed by the seed parent '10.05R.05' (unpatented) and/or the pollen parent '07.09R.47' (unpatented).

The spine color of the seed parent '10.05R.05' (unpatented) is green (RHS green group color near 143 B to 143 A), whereas for the new variety 'Plapink 14116' the color is purplish brown (RHS red group near 183 B to 183 A).

The fruit color of the seed parent '10.05R.05' (unpatented) is yellow (RHS yellow-orange group color near 16 B to 16 A) and the fruit color of pollen parent '07.09R.47' (unpatented) is medium red (RHS red group color near 43 B to 43 A), whereas the fruit of the new variety 'Plapink 14116' is light red (RHS red group near 41 C to 41 B).

The seed parent '10.05R.05' (unpatented) has smaller sized fruit and plug compared to the fruit and plug size of the new variety 'Plapink 14116'.

The leaf of the pollen parent '07.09R.47' (unpatented) shows a light green color (RHS green group near 138 C to 138 B) on the underside and the peduncle shows anthocyanin coloration, whereas the leaf of the new variety 'Plapink 14116' shows a medium green color (RHS red group near 137 B to 137 A) on the underside and anthocyanin coloration of the peduncle is absent.

The pollen parent '07.09R.47' (unpatented) has a smaller sized fruit and plug compared to the fruit and plug size of the new variety 'Plapink 14116'.

COMPARISON TO CLOSEST VARIETY

The new variety is believed to be closest to the variety 'Adelita' (U.S. Plant Pat. No. 25,245), but is distinguished therefrom by the following characteristics possessed by 'Plapink 14116' which are different than, or not possessed by 'Adelita' (U.S. Plant Pat. No. 25,245).

'Adelita' (U.S. Plant Pat. No. 25,245) shows equally three and five leaflets by the leaf, whereas 'Plapink 14116' shows three leaflets by the leaf.

The spine density of 'Adelita' (U.S. Plant Pat. No. 25,245) is sparse, whereas 'Plapink 14116' shows a medium to dense spine density. The differences in density, length and size of the spines at the base of 'Plapink 14116' (designated 14.26R.04) and 'Adelita' (U.S. Plant Pat. No. 25,245) are shown in FIG. 8.

The length of the spines of 'Adelita' (U.S. Plant Pat. No. 25,245) is very short to short, with a medium-sized base, whereas the length of the spines of 'Plapink 14116' is medium to long with a medium- to large-sized based.

The pedicel of 'Adelita' (U.S. Plant Pat. No. 25,245) shows an absence or very few number of spines, whereas the pedicel of 'Plapink 14116' shows many spines. The difference in number of spines in the pedicel of 'Plapink 14116' (designated 14.26R.04) and 'Adelita' (U.S. Plant Pat. No. 25,245) is shown in FIG. 9.

The fruit of 'Adelita' (U.S. Plant Pat. No. 25,245) shows a red color (RHS red group near 47 A to 46 A), whereas the fruit of 'Plapink 14116' shows a light red color (RHS red group near 41 C to 41 B). The difference in fruit color of 'Plapink 14116' (designated 14.26R.04) and 'Adelita' (U.S. Plant Pat. No. 25,245) is shown in FIG. 16.

The fruit of 'Adelita' (U.S. Plant Pat. No. 25,245) is firm with a medium to strong adherence of the fruit to the plug, whereas the firmness of the fruit of 'Plared 14116' is medium to firm with a weak to medium adherence of the fruit to the plug.

The time of beginning of flowering on current season's cane of 'Adelita' (U.S. Plant Pat. No. 25,245) is early to medium, whereas time of beginning of flowering on current season's cane of 'Plapink 14116' is very early to early.

The time of beginning of fruit ripening on current year's cane of 'Adelita' (U.S. Plant Pat. No. 25,245) is early, whereas time of beginning of fruit ripening on current year's cane of 'Plapink 14116' is very early to early.

These differences are maintained during the harvest season.

BRIEF DESCRIPTION OF THE ILUSTRATIONS

The accompanying photographs show typical specimens of the new variety 'PLAPINK 14116' including fruit, foliage and flower, in color as nearly true as it is reasonably possible to make in color illustrations of this character.

The plants depicted in the drawings were planted June 10 in the farm of La Mogalla in Cartaya (Huelva), Spain, about 7° W, 37° N, 45 feet elevation. Photographs were taken in about November 4 and November 12, when there was a minimum temperature of about 7° to 9° Centigrade and a maximum temperature of about 18 to 22° Centigrade.

FIG. 1 and FIG. 2 show several plants of the new variety (designated '14.26R.04') which exhibit an upright plant habit with several light-red colored and conical-shaped fruits.

FIG. 3 and FIG. 4 show the upper side and the underside, respectively, of a complete leaf of the new variety (designated '14.26R.04'). It can be sees that the color of the upper side of the leaf of the new variety (designated '14.26R.04') is a darker green (RHS green group near 141 B to 141 A) and the color of underside of the leaf of the new variety (designated '14.26R.04') is a medium green (RHS green group near 137 B to 137 A). It can also be seen that with respect to the relative position of lateral leaflets in the leaf of the new variety (designated '14.26R.04') they are touching.

FIG. 5 and FIG. 6 show the upper side and the underside, respectively, of a terminal leaflet of the new variety (designated '14.26R.04'). In it we can see that the color of the upper side of the terminal leaflet of the new variety (designated '14.26R.04') is a darker green (RHS green group near 141 B to 141 A) and the underside of the terminal leaflet of the new variety (designated 14.26R.04) is a medium green color (RHS green group near 137 B to 137 A).

FIG. 7 shows that anthocyanin coloration of the apex of the very young shoot during rapid grow period is a greyed-red color (RHS greyed-red near 181 D to 182 D) and the intensity of the anthocyanin coloration is weak.

FIG. 8 shows the current season's cane of the new variety (designated '14.26R.04'), with a medium to dense spine density, medium to long spine length and a base that is medium to large, in comparison with the current season's cane of 'Adelita' (U.S. Plant Pat. No.25,245) which has a sparse density of spines, a very short to short spine length and a medium size base of the spines.

FIG. 9 shows the pedicel of the new variety (designated '14.26R.04') with many spines in comparison with the pedicel of 'Adelita' (U.S. Plant Pat. No. 25,245) with absent or very few spines.

Figure 1:
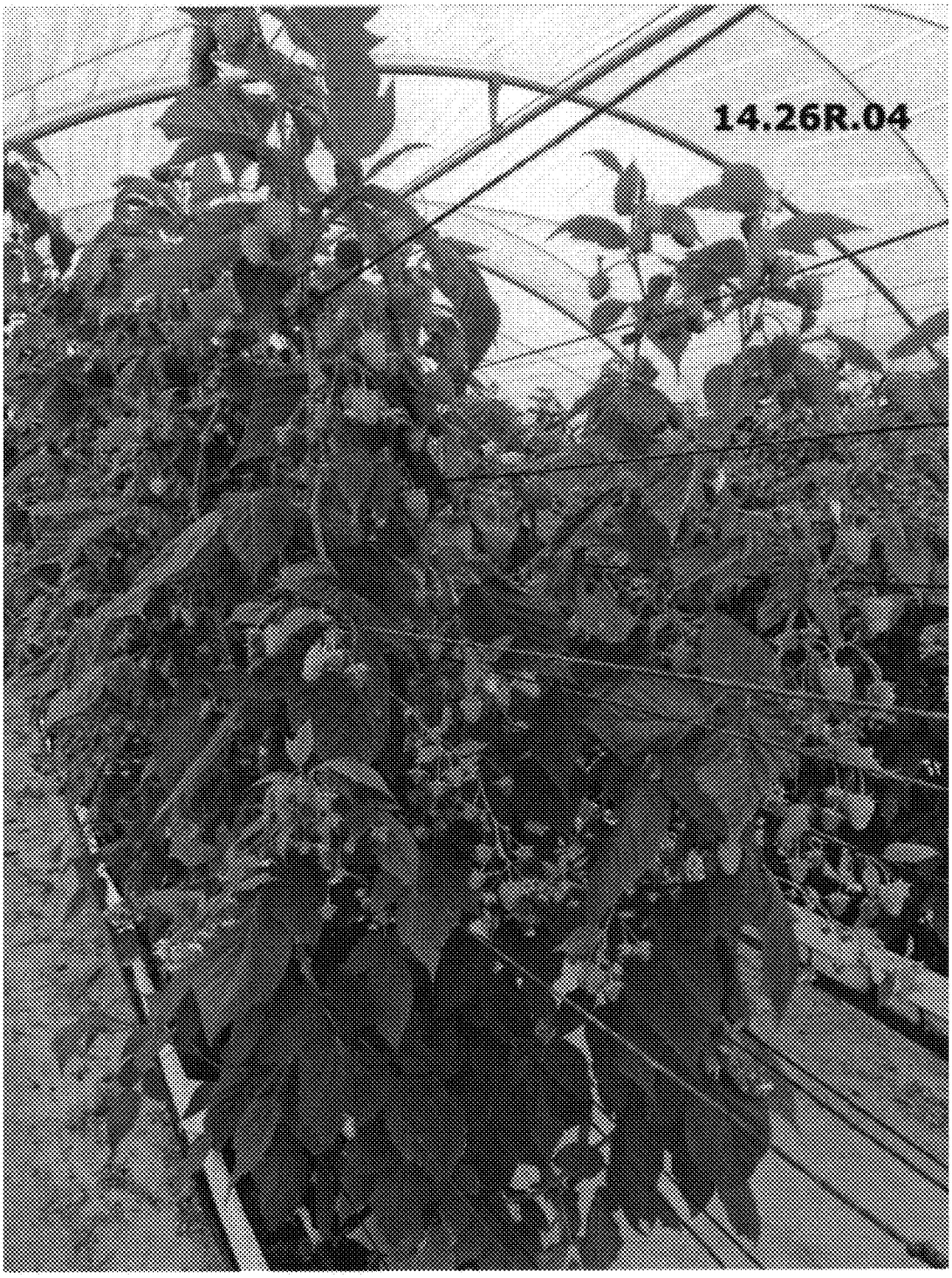
Figure 2:
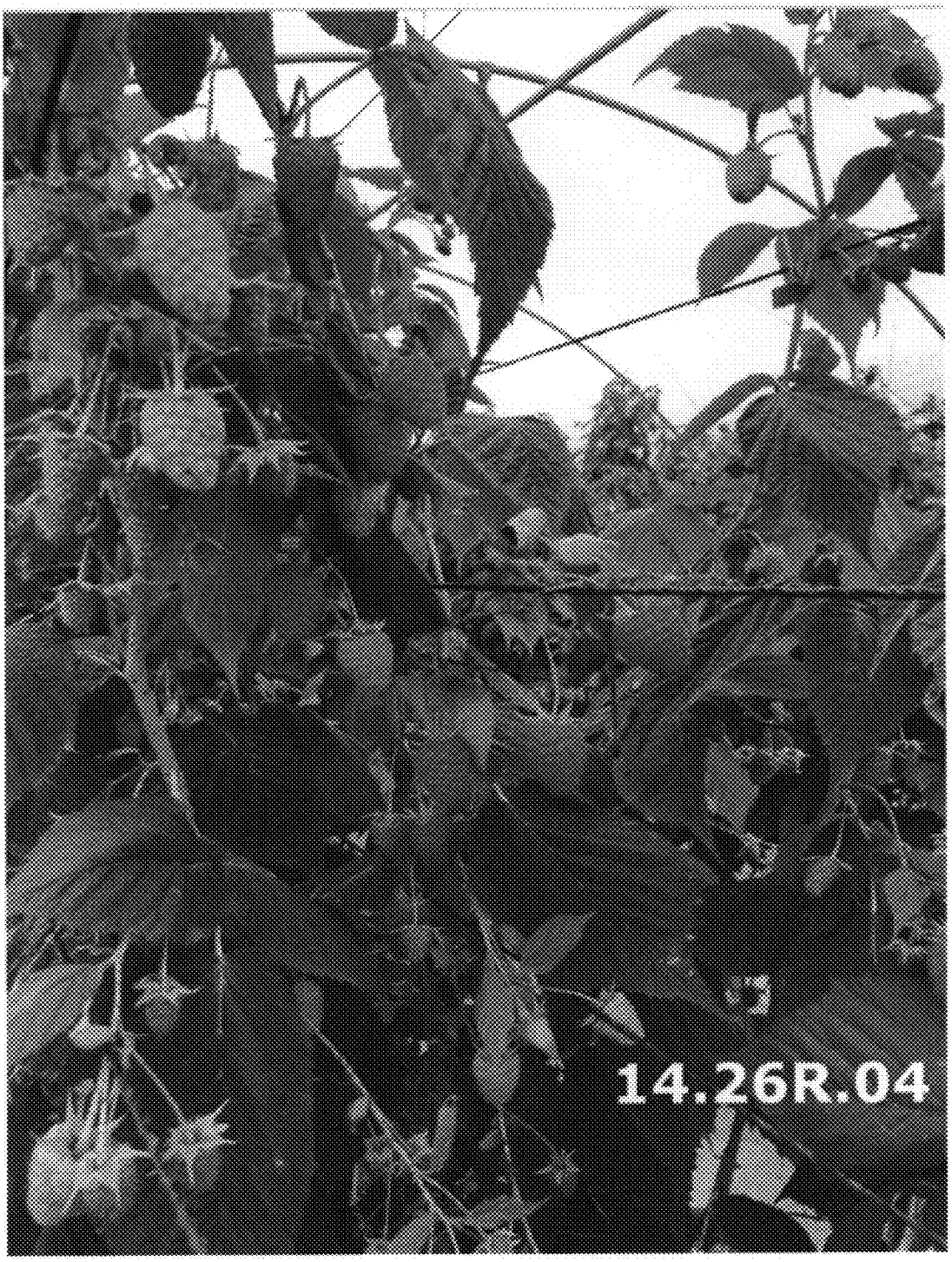
Figure 3:
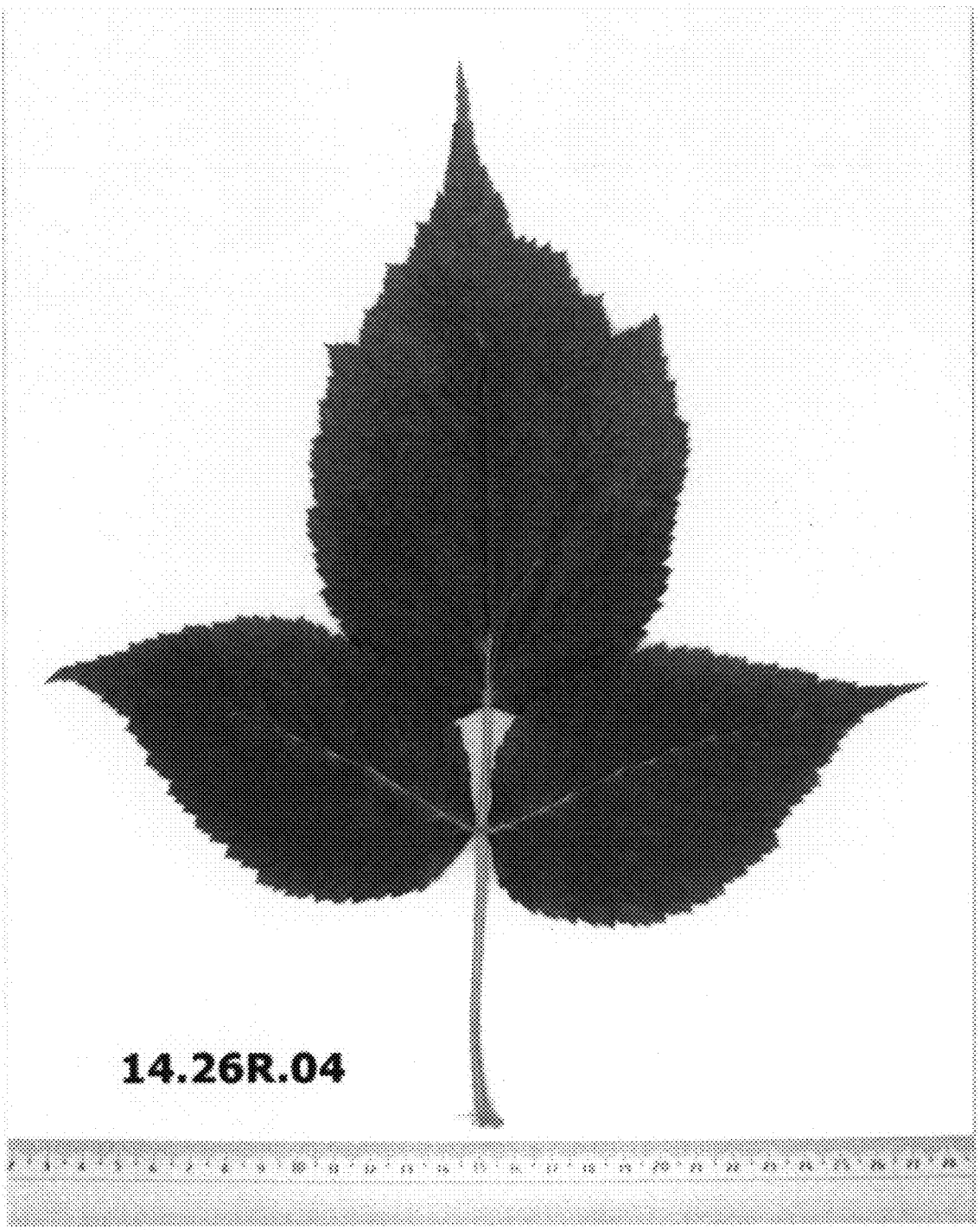
Figure 4:
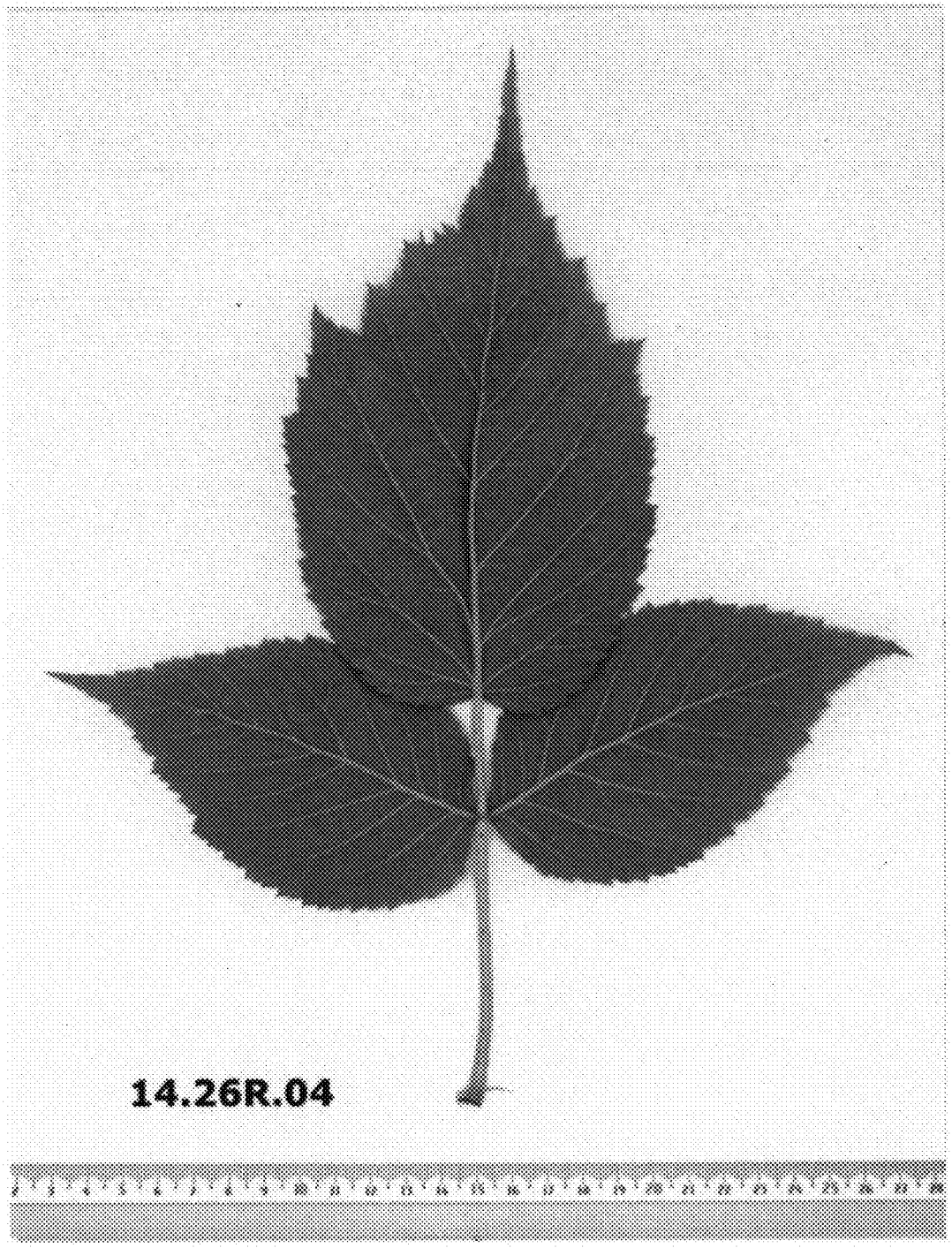
Figure 5:
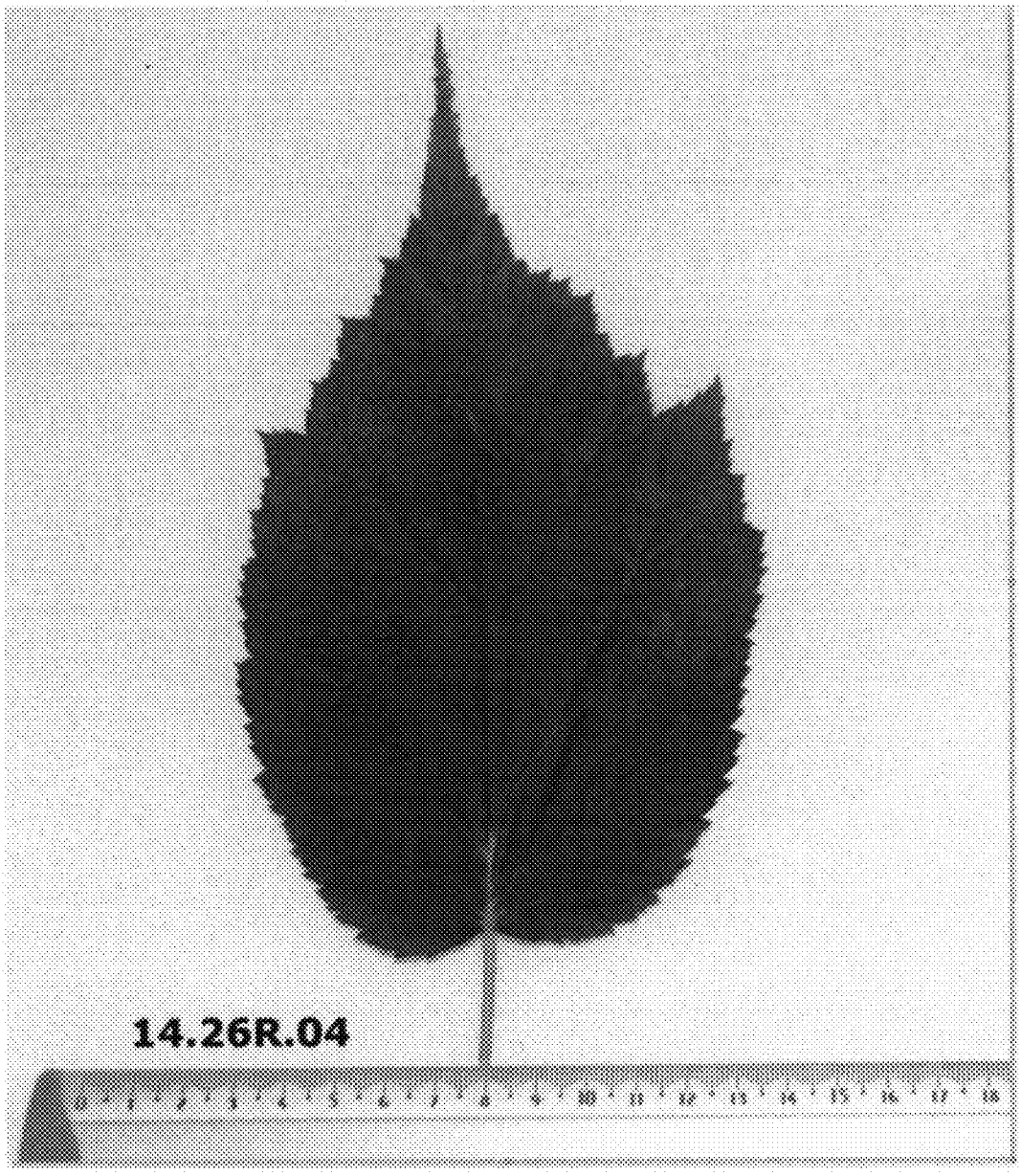
Figure 6:
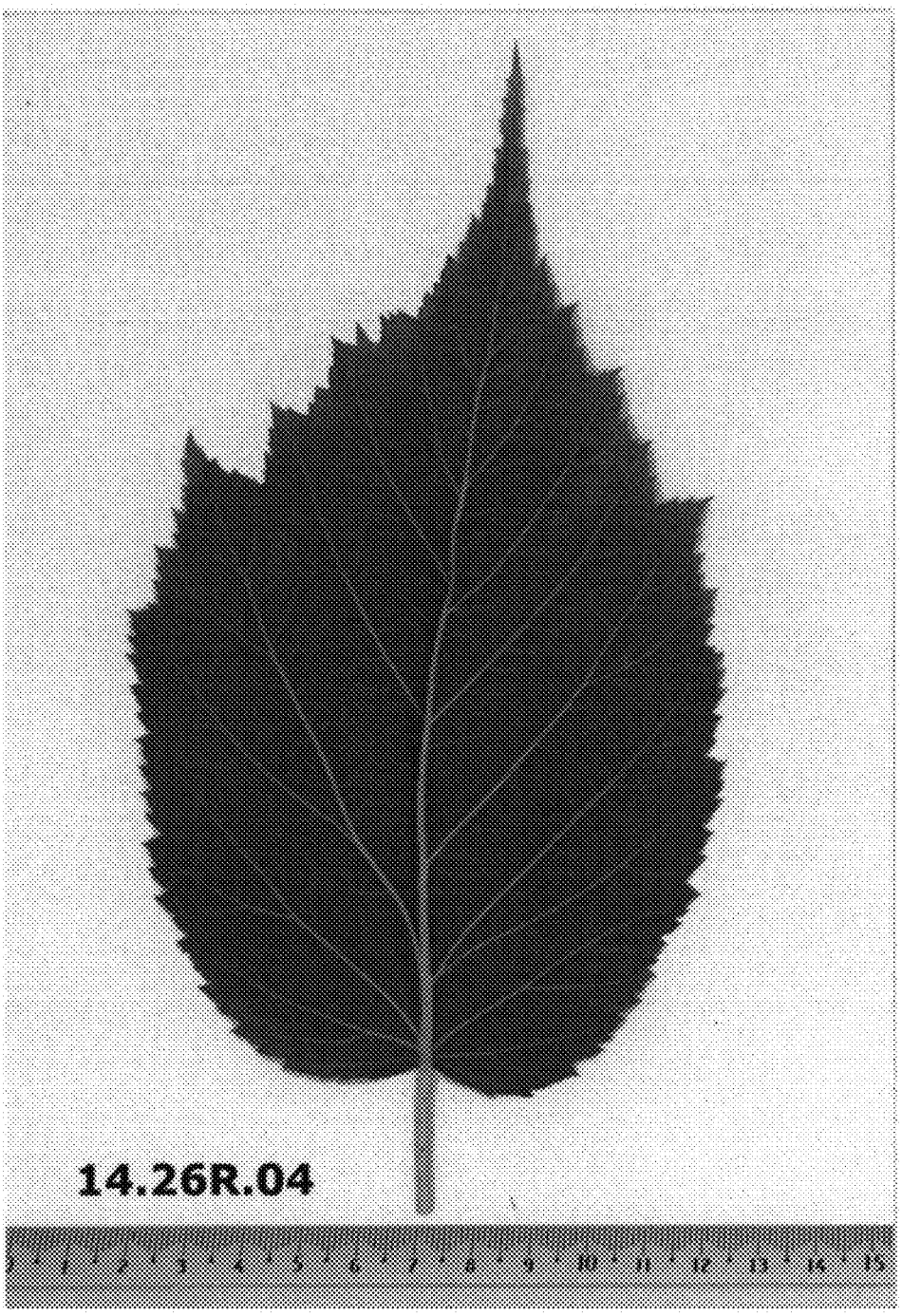
Figure 7:
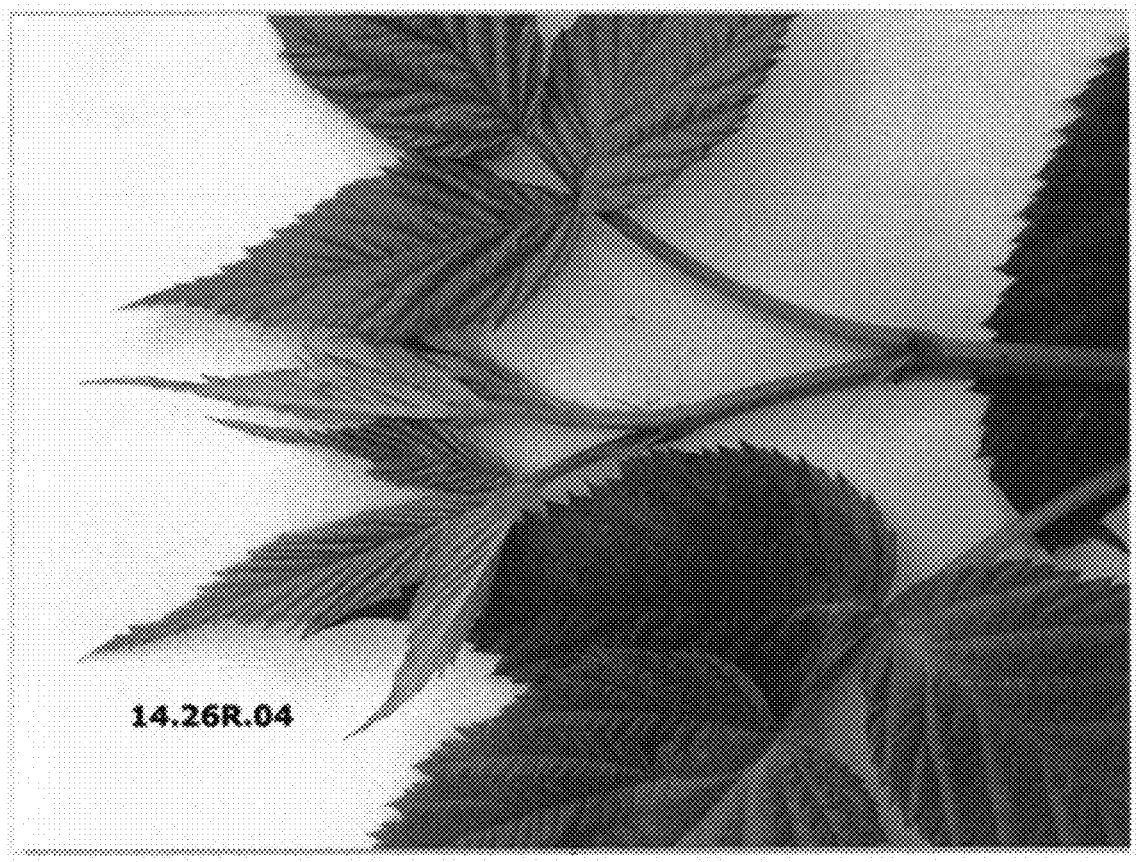
Figure 8:
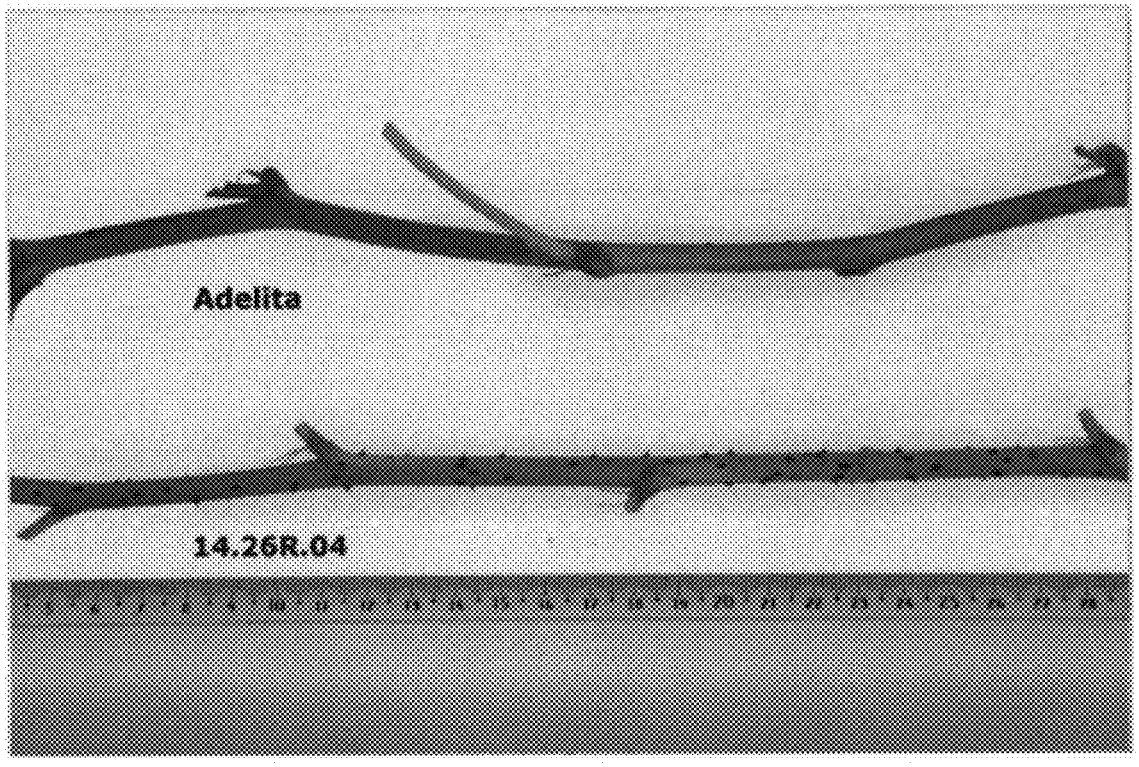
Figure 9:
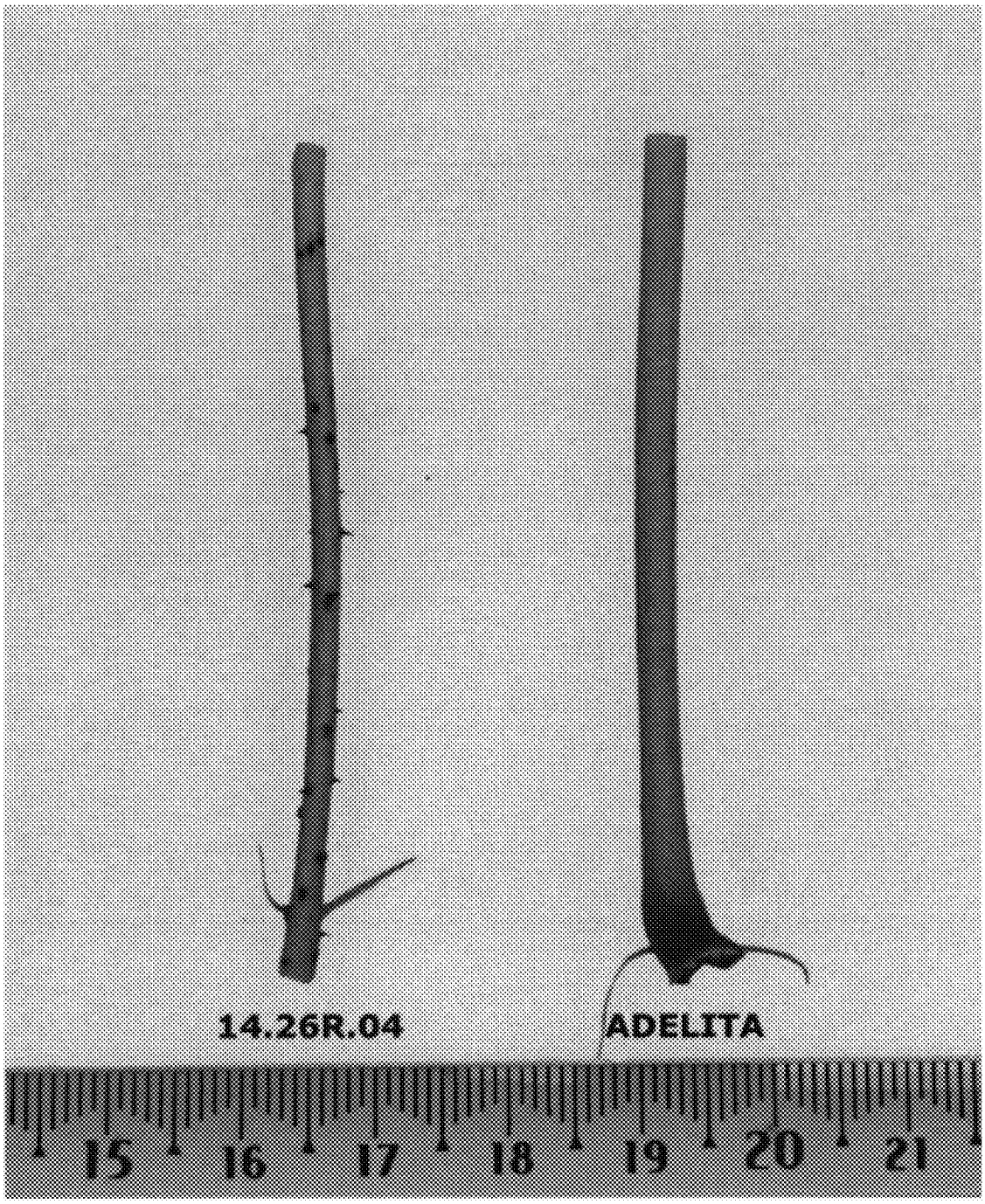
Figure 10:
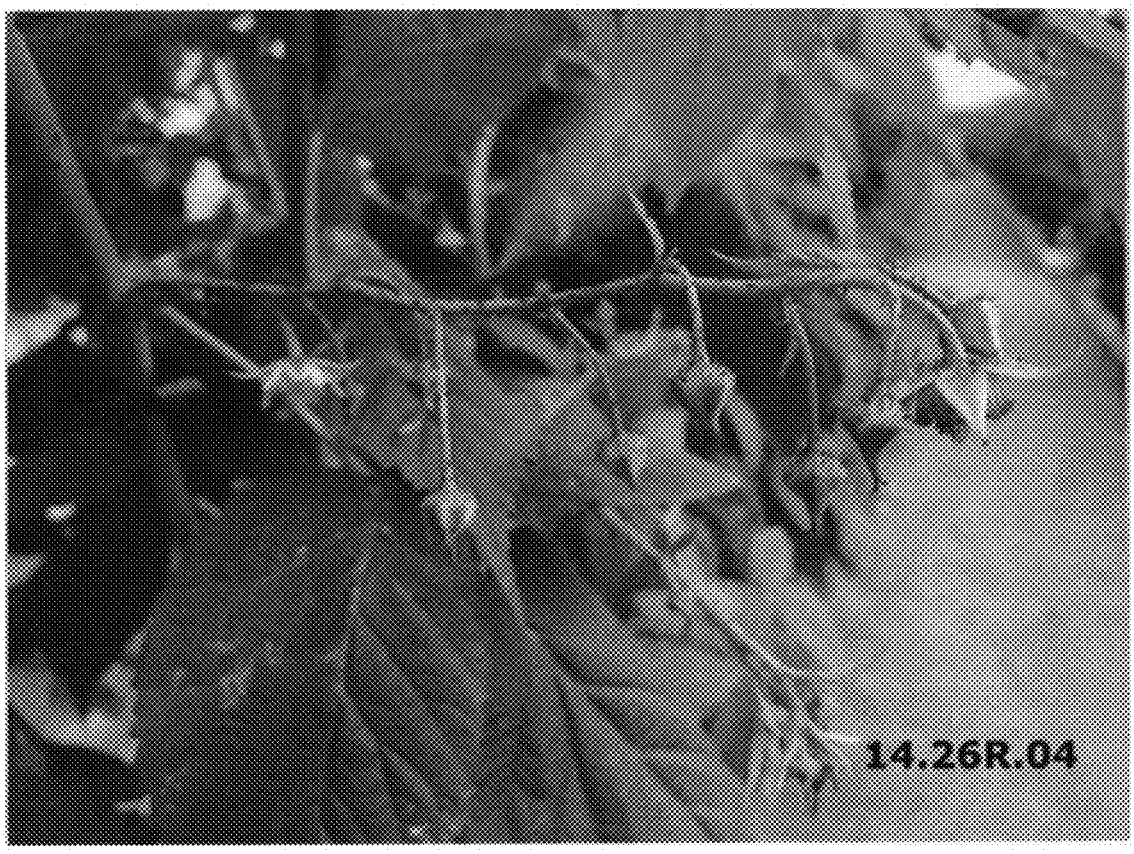
FIG. 10 shows typical flower buds of the new variety (designated '14.26R.04') with trapezoidal shape and green color (RHS green group near 138 D to 138 C).
Figure 11:
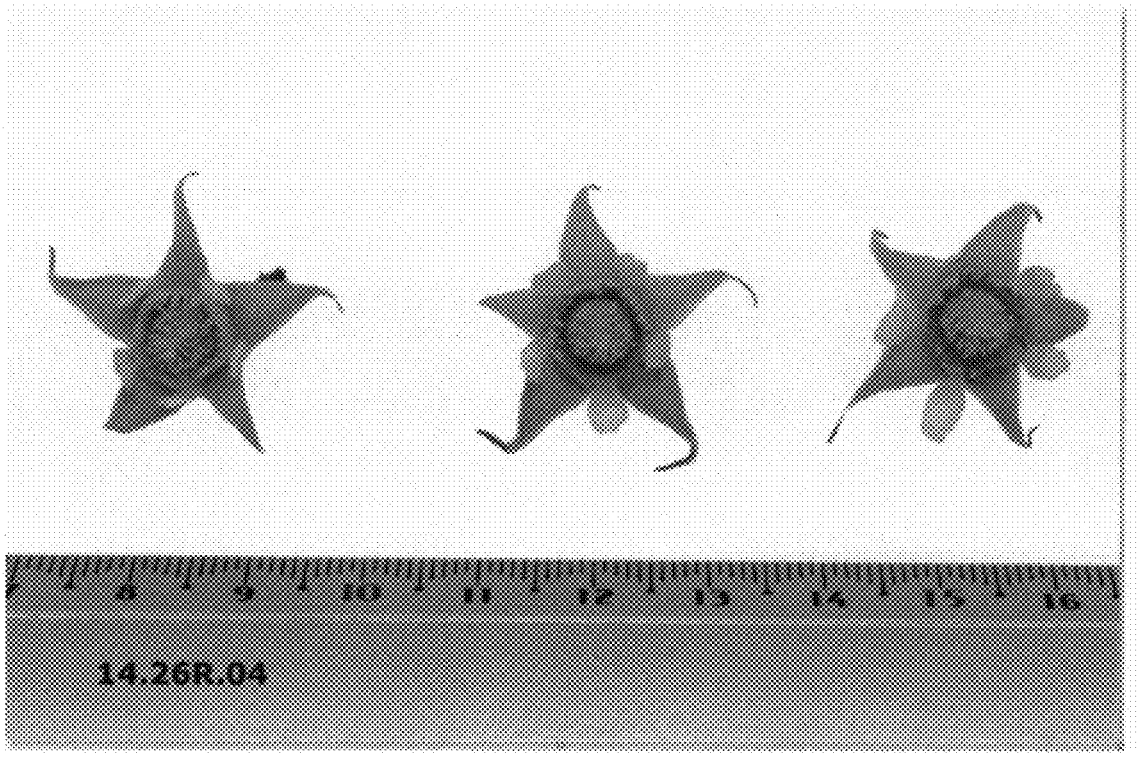
FIG. 11 shows typical flowers of the new variety (designated '14.26R.04').
Figure 12:
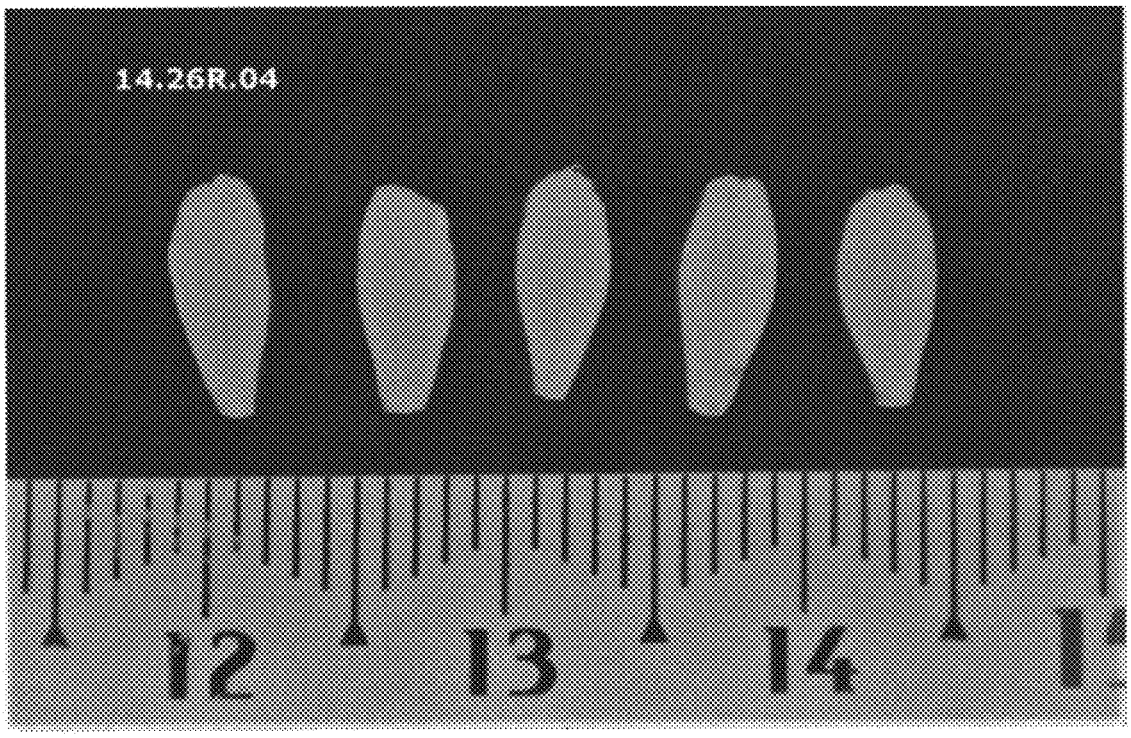
FIG. 12 shows typical petals of the new variety (designated '14.26R.04') with narrow elliptical shape and white color (RHS white group near 155 C to 155 B).
Figure 13:
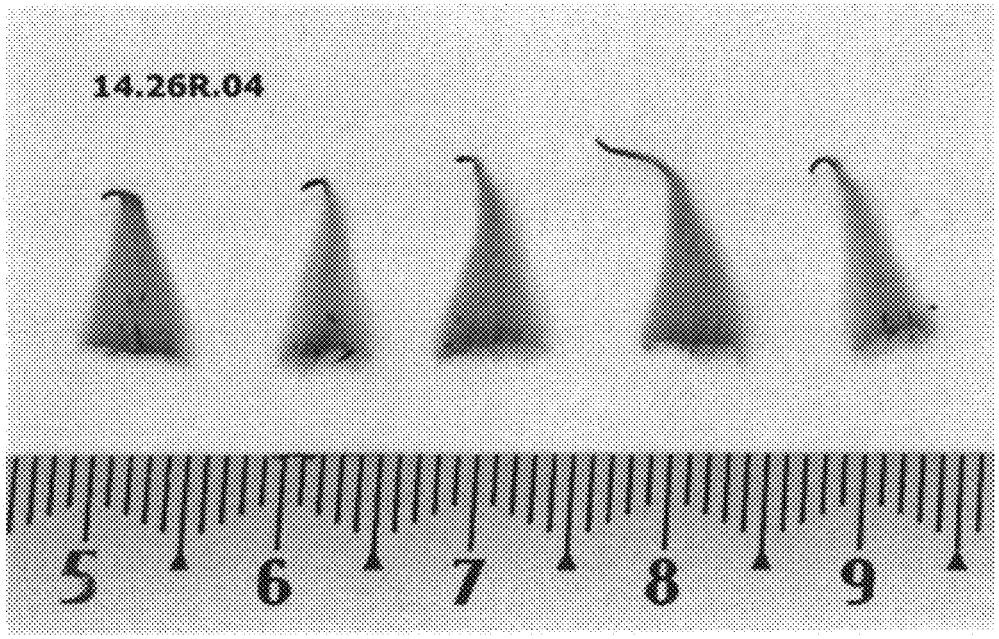
FIG. 13 shows typical sepals of the new variety (designated '14.26R.04') with triangular shape, acuminate apex and green color (RHS green group near 145 B to 145 A).
Figure 14:
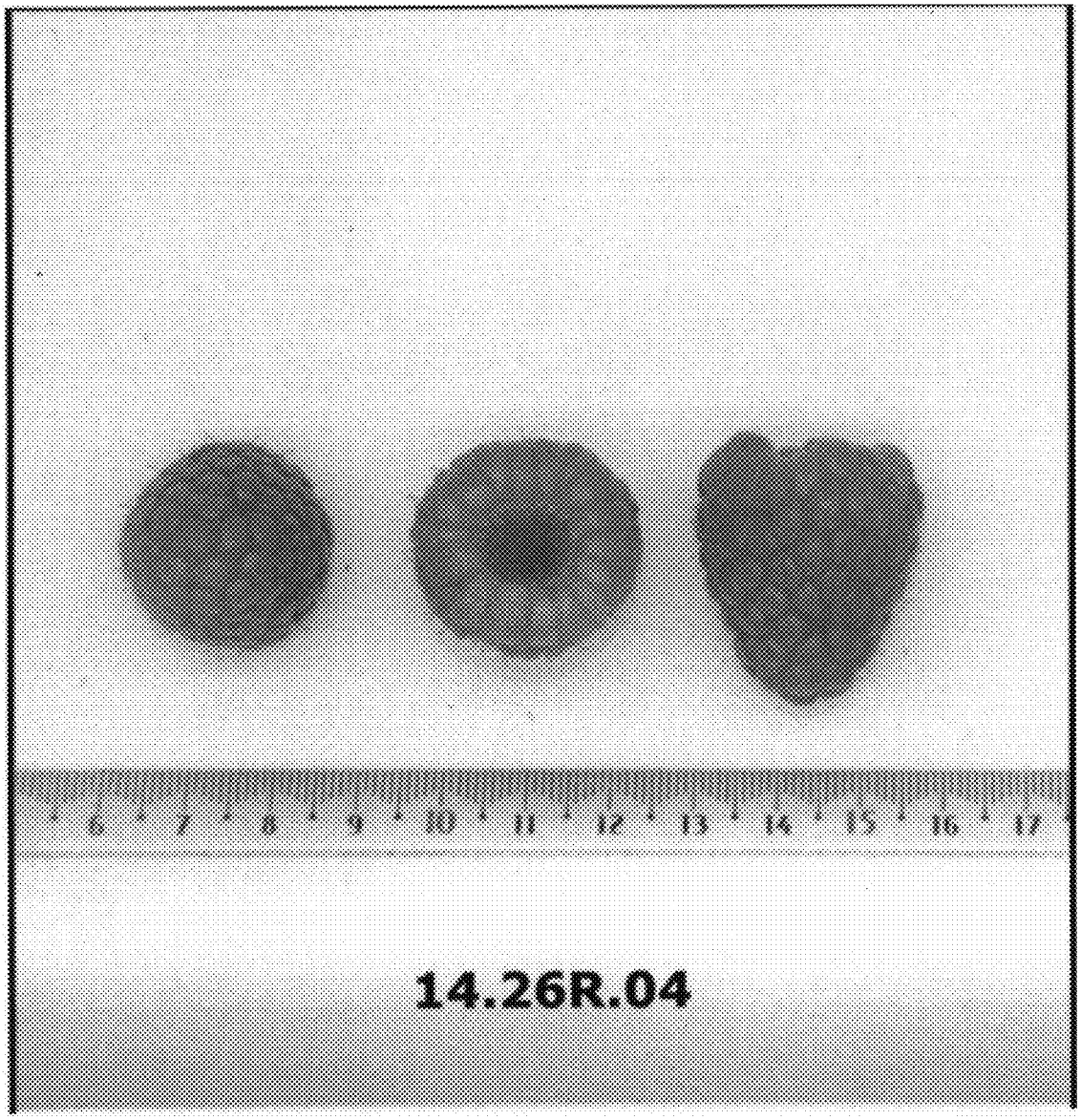
FIG. 14 and FIG. 15 show typical fruits of the new variety (designated '14.26R.04') in lateral view, with conical shape and light red color (RHS red group near 41 C to 41 B).
Figure 15:
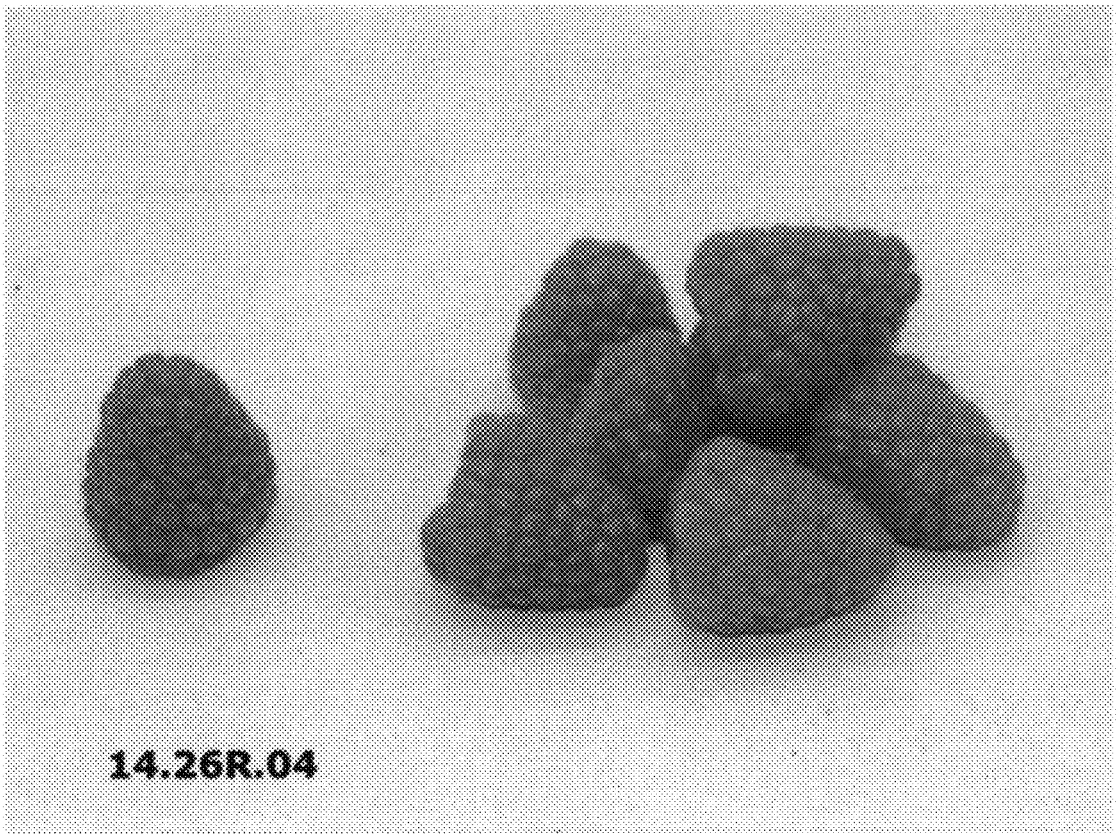
Figure 16:
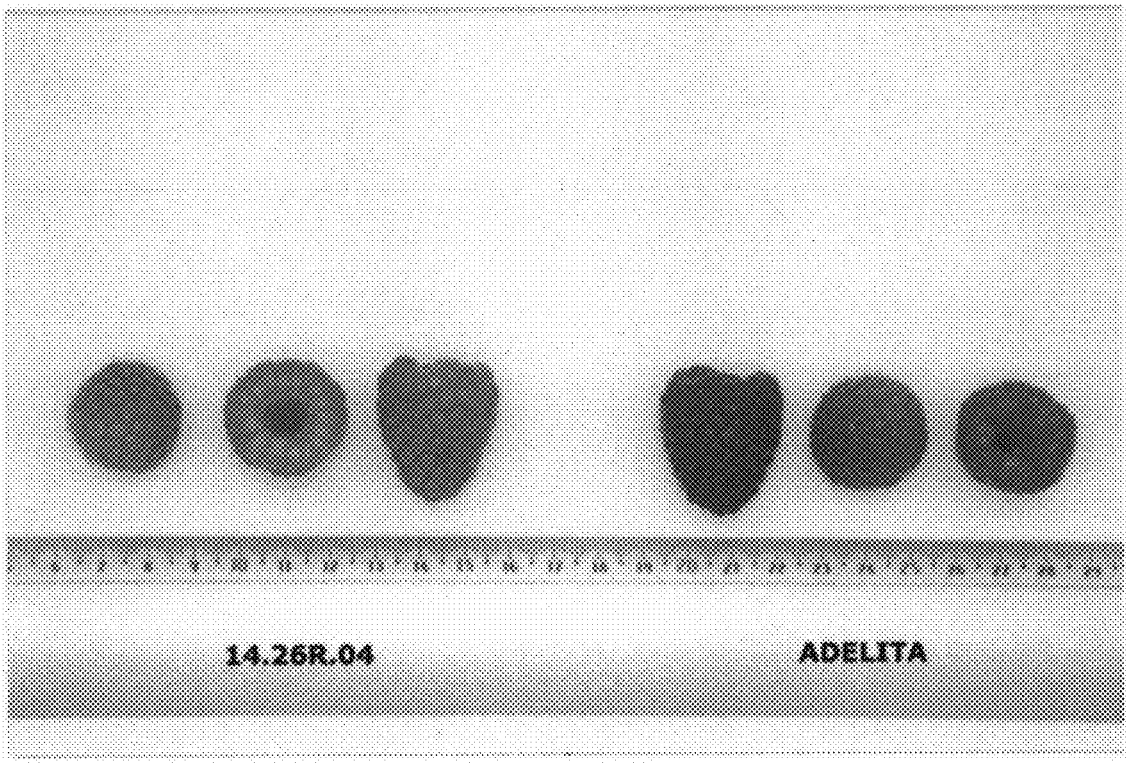

FIG. 16 shows typical fruits of the new variety (designated '14.26R.04') with a light red color (RHS red group near 41 C to 41 B) in comparison with typical fruits of 'Adelita' (U.S. Plant Pat. No. 25,245) with a medium red color fruit (RHS red group near 47 A to 46 A).

Figure 17:
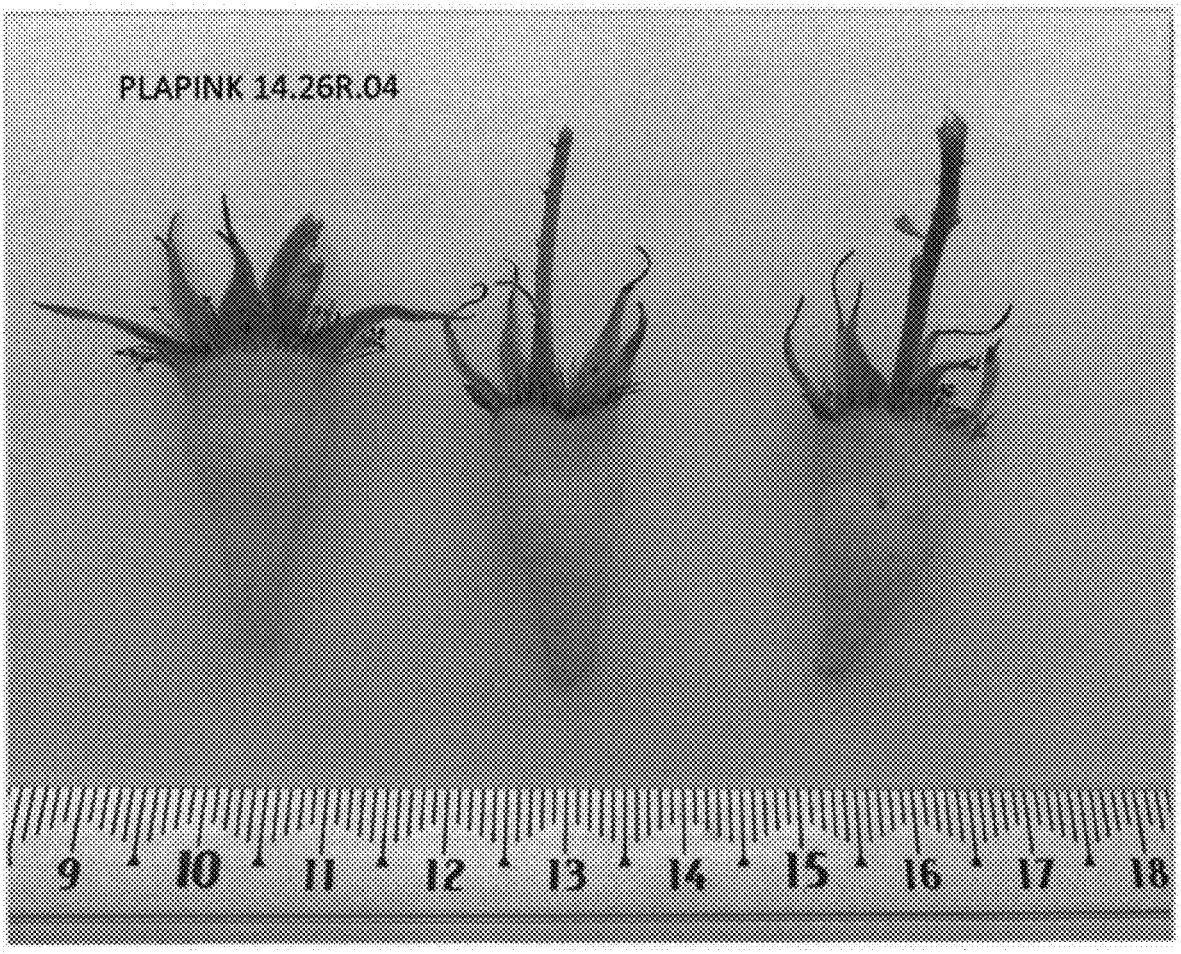

FIG. 17 shows typical receptacles of fruit the new variety (designated '14.26R.04') with conical shape and greyed-yellow color (RHS greyed-yellow group near 161 D to 161 C).

DESCRIPTION OF THE NEW VARIETY

The following detailed description of the new variety is based upon observations taken of plants and fruits grown "underglass", i.e. under tunnel, in the farm of La Mogalla in Cartaya (Huelva), Spain, 7° W., 37° N., 45 feet elevation. Water and fertilizer were applied through drip irrigation. The primocane production observations were made in Huelva (Spain) between Jun. 10, 2019 and Jun. 9, 2020. 'Plapink 14116' is a primocane variety, with consistent fruit production from the beginning of October through the end of December on primocanes and in the ensuing year the beginning of April through the beginning of June.

The following description is in accordance with UPOV terminology and the color terminology herein is in accordance with The Royal Horticultural Society Colour Chart (R.H.S.C.C.), 3rd edition published in 1995. The color descriptions and other phenotypical descriptions may deviate from the stated values and descriptions depending upon variation in environmental, seasonal, climatic, and culture conditions.

PROPAGATION

The new variety is principally propagated by way of root cuttings. Although propagation by root cuttings is presently preferred, other know methods of propagating raspberry plants may be used. Raspberries root and develop well after transplanting.

'Plapink 14116' is a primocane variety with fruit production from the beginning of October through the end of December on primocanes and in the ensuing year beginning in April and beginning in June. It is a self-fertile variety. It produces a large quantity of pollen throughout the seasons and pollination is good.

Trials were pursued in in Cartaya (Huelva), Spain. The plants described are from high elevation nursery in Segovia, Spain, 3° 59'W., 41° 22'N., 2742 feet elevation. Plants were planted on June 12 in the first year and June 10 in the second year with a sample size of 2 repetitions every year and 120 plants per repetition per year.

GENERAL

TABLE 1

Table 1 shows the accumulated production of 1st Quality Fruit (g/plant) of the new variety 'Plapink 14116' when compared to varieties 'Adelita' and 'Lupita' (PP25.171).

| Variety | Middle of September through end of December | Beginning in April through beginning of June | Total |
|---|---|---|---|
| 'Plapink 14116' | 1946.70 | 1376.60 | 3223.30 |
| 'ADELITA' | 1681.10 | 1086.70 | 2767.80 |
| 'LUPITA' | 1027.90 | 1636.60 | 2664.50 |

TABLE 2

Table 2 shows the Accumulated Total Yield of 1st and 2nd quality fruit (g/plant) of the new variety 'Plapink 14116' when compared to varieties 'Adelita' and 'Lupita'.
Accumulated total yield: 1st and 2nd quality fruit (grames/plant)

| Variety | 1st + 2nd Quality Middle of September through end of December | 1st + 2nd Quality Beginning in April through beginning of June | Total |
|---|---|---|---|
| 'Plapink 14116' | 2120.50 | 1631.80 | 3752.30 |
| 'ADELITA' | 1942.80 | 1369.20 | 3312.00 |
| 'LUPITA' | 1121.40 | 1662.60 | 2784.00 |

TABLE 3

Table 3 shows the production from the beginning of September through the end of December of First Quality Fruit (1st quality) and Second Quality Fruit (2nd quality) in g/plant, of the new variety 'Plapink 14116' when compared to varieties 'Adelita' and 'Lupita'.

| Variety | 1st Quality | 2nd Quality | TOTAL (1st Quality + 2nd Quality) | % 2nd Quality |
|---|---|---|---|---|
| 'Plapink 14116' | 1946.70 | 173.80 | 2120.50 | 8.19 |
| 'ADELITA' | 1681.10 | 261.70 | 1942.80 | 13.47 |
| 'LUPITA' | 1027.40 | 93.50 | 1121.40 | 8.33 |

% 2nd Quality = (2nd Quality/TOTAL) × 100

TABLE 4

Table 4 shows production from the beginning of April through the beginning of June of First Quality Fruit (1st quality) and Second Quality Fruit (2nd quality) in g/plant, of the new variety 'Plapink 14116' when compared to the varieties 'Adelita' and 'Lupita'.

| Variety | 1st Quality | 2nd Quality | TOTAL (1st Quality + 2nd Quality) | % 2nd Quality |
|---|---|---|---|---|
| 'Plapink 14116' | 1376.60 | 255.20 | 2030.10 | 15.60 |
| 'ADELITA' | 1086.70 | 282.50 | 1631.80 | 20.60 |
| 'LUPITA' | 1636.60 | 26.00 | 1662.60 | 1.56 |

% 2nd Quality = (2nd Quality/TOTAL) × 100

TABLE 5

Table 5 shows the weight (g/Fruit) in two production periods: September to December, and April to June of the new variety 'Plapink 14116' when compared to the varieties 'Adelita' and 'Lupita'.

| Variety | Middle of September to end of December | Beginning April to beginning June |
|---|---|---|
| 'Plapink 14103' | 6.5-6.0 | 6.2-5.8 |
| 'ADELITA' | 7.4-6.1 | 5.0-4.1 |
| 'LUPITA' | 5.4-4.7 | 4.9-4.1 |

WEIGHT is shown as the average weight per fruit (g/fruit) in First Quality Fruits.

TABLE 6

Table 6 shows a comparison of an analysis of the fruit from the new variety 'Plapink 14116' and the varieties 'Adelita' and 'Lupita'.
FRUIT ANALYSIS

| | 'Adelita' | 'Plapink 14116' | 'Lupita' |
|---|---|---|---|
| Humidity & Volatile Matter (%) | 86.2 | 86.8 | 89.2 |
| Dry Matter (%) | 13.8 | 13.0 | 10.8 |
| pH (to 20°) | 3.00 | 3.2 | 3.1 |
| Acidity as Anhydride Citric (%) | 2.4 | 2 | 2,2 |
| Soluble Solids (°Brix) | 10.9 | 9.2 | 9.00 |
| Maturity Index | 4.5 | 4.7 | 4.1 |
| Content in Ascorbic Acid (ppm) | 261 | 258 | 259 |
| Dominant Tonality (nm) | 515 | 515 | 515 |
| Luminosity: Transmittance to 460 nm | 22.65 | 30.85 | 23.3 |

The following definitions apply:

Dry Matter refers to the residual weight left from the trituration of the fruit after the drying process at a temperature of 103° C.±2° C. until reaching constant weight. (%) Dry Matter=(Weight Dry Matter/Weight Fresh Matter)×100

Humidity & Volatile Matter represents the content in volatile matters and water of the fruits. (%) Humidity & Volatile Matter=100−% Dry Matter Maturity Index refers to the relation between Soluble solids and Acidity as Anhydride Citric.

Maturity Index=Soluble solids/Acidity as Anhydride Citric

DETAILED DESCRIPTION OF THE NEW VARIETY

The following additional information is provided to further describe the new variety. Data is from plants growing in containers of 48 liters of capacity and they are described during cultivar's primocane.

PLANT

*Habit.*—Upright.
*Vigor.*—Medium.

Cultivar's primocane cane:
- *Length.*—Approximately 240 cm to 290 cm.
- *Diameter.*—Approximately 0.9 to 1.3 cm.
- *Texture.*—Smooth.
- *Internode length.*—Approximately 5.8 cm to 7.1 cm.
- *Cross section.*—Rounded.
- *Pubescence.*—Absent.
- *Anthocyanin coloration of apex during rapid grow period.*—About RHS greyed-red color near 181 D to 182 D.
- *Cane color.*—About RHS green group near 143 D to 143 C.

Spines:
- *Shape.*—Conical.
- *Density.*—Medium to dense.
- *Number/cm.*—about 4 to 6.
- *Length.*—Approximately 0.10 cm to 0.15 cm.
- *Width.*—Approximately 0.15 cm to 0.25 cm at the base.
- *Apex.*—Slightly curved.
- *Color.*—About RHS greyed-purple group color near 183 B to 183 A.
- *Flexibility.*—Medium.

Leaf:
- *Type.*—Compound.
- *Number of leaflets.*—3.
- *Arrangement of lateral leaflets.*—Touching.
- *Overlapping of lateral leaflets with terminal leaflet.*—Present.
- *Upperside color.*—About RHS green group color near 141 B to 141 A.
- *Underside color.*—About RHS green group color near 137 B to 137 A.
- *Length.*—Approximately 24.5 cm to 25.5 cm.
- *Width.*—Approximately 18.0 cm to 19.5 cm.
- *Profile of leaflets in cross section.*—Straight.
- *Relief between veins.*—Medium.

Lateral leaflet:
- *Shape.*—Elliptic.
- *Length.*—Approximately 6.5 cm to 7.5 cm.
- *Width.*—Approximately 3.5 cm to 4.0 cm.
- *Shape of tip.*—Acuminate.
- *Shape of base.*—Obtuse.
- *Shape of margin.*—Double serrate.
- *Upperside rugosity.*—Medium.
- *Underside texture.*—Smooth.
- *Upperside color.*—About RHS green group color near 141 B to 141 A.
- *Underside color.*—About RHS green group color near 137 B to 137 A.
- *Venation pattern.*—Reticulate or penniveined.
- *Upperside venation coloration.*—About RHS yellow-green group color near 144 D to 144 C.
- *Underside venation coloration.*—About RHS yellow-green group color near 144 B to 144 A.

Terminal leaflet:
- *Length/width ratio.*—Longer than broad.
- *Length.*—Approximately cm 16.5 to 18.5cm.
- *Width.*—Approximately 10.0 cm to 10.5 cm.
- *Cross section.*—Straight.
- *Upperside color.*—About RHS green group color near 141 B to 141 A.
- *Underside color.*—About RHS green group color near 137 B to 137 A.
- *Shape of leaflet.*—Ovate.
- *Shape of tip.*—Acuminate.
- *Shape of base.*—Rounded.
- *Shape of margin.*—Double serrate.
- *Upperside rugosity.*—Medium.
- *Underside texture.*—Smooth.
- *Venation pattern.*—Reticulate or penniveined.
- *Upperside venation coloration.*—About RHS yellow-green group color near 144 D to 144 C.
- *Underside venation coloration.*—About RHS yellow-green group color near 144 B to 144 A.

Rachis:
- *Length between the terminal leaflet and adjacent lateral leaflet.*—Approximately 3.0 cm to 3.5 cm.
- *Coloration.*—About RHS yellow green group color near 144 D to 145 C.

Petiole:
- *Color.*—About RHS yellow green group color near 145 B to 145 A.
- *Petiolule length.*—Approximately 7.0 cm to 7.5 cm.
- *Petiole length (rachis with petiolule).*—Approximately 10.0 cm to 11.0 cm.
- *Diameter.*—Approximately 2.0 mm to 2.5 mm in the Petiolule and Approximately 1.5mm to 2.0 mm in the rachis.
- *Spines.*—Medium.
- *Petiole texture.*—Smooth.

Stipule:
- *Quantity per leaf.*—2.
- *Shape.*—Erect.
- *Length.*—Approximately 7.0 mm to 9.0 mm.
- *Width.*—Very narrow, approximately 0.2 mm to 0.3 mm.
- *Color (both surfaces).*—About RHS yellow green group color near 145 C to 145 B.

Flower bud:
- *Shape.*—Trapezoidal.
- *Diameter.*—Approximately 1.0 cm to 1.5 cm.
- *Length.*—Approximately 1.3 cm to 1.8 cm.
- *Color.*—About RHS green group near 138 D to 138 C.

Pedicel:
- *Length.*—Approximately 3.9 cm to 4.4 cm.
- *Diameter.*—Approximately 2.2 mm to 2.6 mm.

*Pedicel color.*—About RHS green group near 143 D to 143 C.
*Surface texture.*—Smooth.
*Density of spines.*—Many.

FLOWER

*Diameter.*—Approximately 1.2 cm to 1.6 cm.
*Number of pistils per flower.*—About 75 to 90.
*Pistil length.*—Approximately 3.5 mm to 4.0 mm.
*Ovary shape.*—Pyriform.
*Ovary length.*—Medium.
*Ovary width.*—Narrow.
*Ovary color.*—About RHS green group color near 142 D to 142 C.
*Style length.*—Approximately 0.10 cm to 0.15 cm.
*Style color.*—About RHS yellow-green group color near 145 D.
*Number of stamens per flower.*—About 90 to 110.
*Stamen length.*—Approximately 0.3 cm to 0.4 cm.
*Stamen shape.*—Cylindrical lengthened.
*Stamen color.*—About RHS green-white group color near 157 D to 157 C.
*Pollen:amount.*—Moderate.
*Pollen color.*—About RHS yellow green group color near 153 D to 153 C.

Petal:
*Number of petals per flower.*—About 5.
*Shape.*—Narrow elliptical.
*Length.*—Approximately 7.0mm to 8.0 mm.
*Width.*—Approximately 2.5 mm to 3.5 mm.
*Apex shape.*—flat rounded.
*Base shape.*—Narrow.
*Margin.*—Smooth and regular.
*Texture.*—Smooth.
*Color (both surfaces).*—About RHS white group color near 155 C to 155 B.

Sepal:
*Number of sepals per flower.*—About 5.
*Shape.*—Triangular.
*Length.*—Approximately 7.0 mm to 9.5 mm.
*Width.*—Approximately 5.0 mm to 6.0 mm.
*Apex shape.*—Acuminate.
*Base shape.*—large at the base forming the calyx.
*Margin.*—Smooth and regular.
*Texture.*—Smooth.
*Color.*—About RHS green group color near 145 B to 145 A.

Peduncles:
*Length.*—Approximately 16.5 cm to 18.5 cm.
*Diameter.*—Approximately 4.0 mm to 4.5 mm.
*Surface texture.*—Smooth.
*Density of spines.*—Medium to many.
*Color.*—About RHS green group near 143 D to 143 C.

FRUIT

*Shape.*—Conical.
*Length.*—Approximately 2.8 cm to 3.2 cm.
*Width.*—Approximately 2.2 cm to 2.6 cm.
*Color.*—About RHS red group color near 41 C to 41 B.
*Number of drupelets per fruit.*—About 90 to 95.
*Size of single drupelet.*—Approximately 0.40 cm to 0.45 cm.
*Drupelet arrangement around the berry.*—Slightly irregular.
*Glossiness.*—Strong.
*Firmness.*—Medium to Firm.
*Adherence to plug.*—Weak to Medium.
*Diameter hollow center.*—Approximately 1.0 cm to 1.3 cm.

Receptacle:
*Length.*—Approximately 2.0 cm to 2.5 cm.
*Diameter.*—Approximately 0.9 cm to 1.2 cm.
*Shape.*—Conical.
*Color.*—About RHS greyed-yellow group near 161 D to 161 C.

Seed:
*Number of seeds per drupelet.*—1.
*Shape.*—Slightly reniform.
*Color.*—About RHS greyed-orange group near 164 D to 164 C.
*Surface texture.*—Wrinkled.

Fruit bearing type: Both on previous year's cane in summer and on current year's cane in autumn.

Fruiting lateral cane:
*Number of fruit per fruiting lateral cane.*—About 18 to 25 fruits.
*Average number of fruit per node.*—1 fruit.

GENERAL

Date of planting: About June 10 in the farm of La Mogalla, in Cartaya (Huelva), Spain, about 7° W, 37° N, 45 feet elevation.

Time of flowering data: 10% flowering on primocane occurs about August 23 with first mature fruits are about September 27 (15-20 g/plant), with a maximum production at the beginning of November.

STORAGE QUALITIES

'Plapink 14116' fruit maintains their quality characteristics when keeping them in a frigo chamber at temperatures of about 2° C. during 48 hours. The fruit's color remains substantially the same. Self life of 'Plapink 14116' is good.

USE/MARKET

The berries of 'Plapink 14116' are suitable for consumption as fresh fruit. Also, they are suitable to processing.

DISEASE RESISTANCE

No particular sensitivity to any disease or pest has been observed for 'Plapink 14116'.

What is claimed is:

1. A new and distinct variety of raspberry plant named 'PLAPINK 14116' as herein described and illustrated.

* * * * *